United States Patent [19]

Koenig et al.

[11] 4,010,165

[45] Mar. 1, 1977

[54] MANUFACTURE OF THIOPHEN-3-ALDEHYDE

[75] Inventors: Horst Koenig; Ulrich Ohnsorge, both of Ludwigshafen, Germany

[73] Assignee: BASF Aktiengesellschaft, Ludwigshafen (Rhine), Germany

[22] Filed: Sept. 24, 1975

[21] Appl. No.: 616,447

[30] Foreign Application Priority Data

Oct. 3, 1976 Germany ............................ 2447253

[52] U.S. Cl. ............................................ 260/332.3 R
[51] Int. Cl.² ............................................ C07D 333/16
[58] Field of Search ................... 260/332.3 R, 332.8

[56] References Cited

UNITED STATES PATENTS 3,819,651  6/1974  Worbs et al. .................... 260/332.8

Primary Examiner—James O. Thomas, Jr.
Assistant Examiner—A. Siegel
Attorney, Agent, or Firm—Johnston, Keil, Thompson & Shurtleff

[57] ABSTRACT

A process for the manufacture of thiophen-3-aldehyde, in which a 2,5-dialkoxy-3-formyl-tetrahydrofuran is reacted with hydrogen sulfide in the presence of a strong acid, at temperatures of from 50° to 320° C.

10 Claims, No Drawings

MANUFACTURE OF THIOPHEN-3-ALDEHYDE

The present invention relates to a process for the manufacture of thiophen-3-aldehyde (3-thenal), wherein a 2,5-dialkoxy-3-formyl-tetrahydrofuran of the formula I

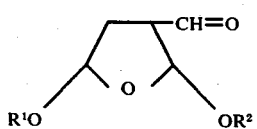

in which $R^1$ $R^2$ are identical or different and each is straight-chain or branched alkyl of 1 to 5 carbon atoms, is reacted with hydrogen sulfide in the presence of a strong acid at elevated temperatures, in one step or two steps.

The following equation illustrates the reaction:

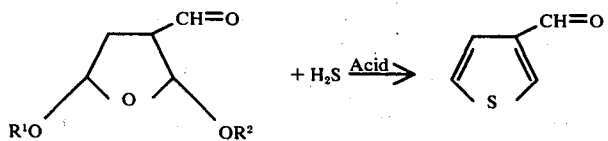

For simplicity, formula I also represents the tautomer of the formula II, which is produced from a compound of the formula I by enolization and which can exist in a cis-form and a trans-form.

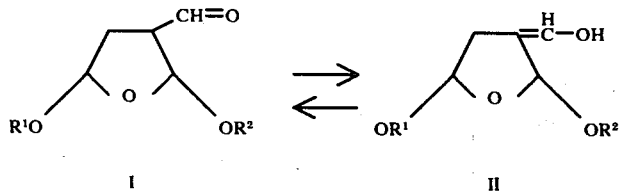

The synthesis of the starting compounds of the formula I has been disclosed. The 2,5-dialkoxy-2,5-dihydrofurans of the formula III may be obtained from furan by the method disclosed by Clauson-Kaas in Acta Chem. Scand., 2 (1948), 109, and their hydroformylation with rhodium triphenylphosphine catalyst by the method of H. Plieninger, Synthesis (1973), 423, gives the compound of the formula I in good yield.

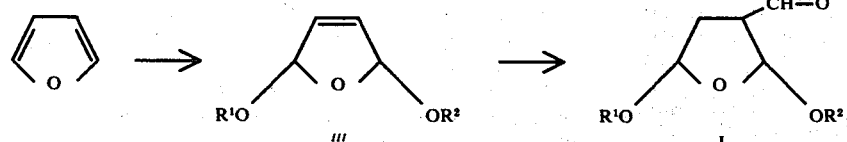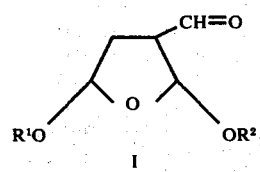

According to the invention, a 2,5-dialkoxy-3-formyl-tetrahydrofuran of the formula I is reacted with hydrogen sulfide in the presence of strong acids, which are to be understood as acids of which the pK in aqueous solution is at most 5.0, and preferably less than 3.0, to give 3-thenal.

The reaction may be carried out under atmospheric pressure or superatmospheric pressure. In the former case, a suitable method is to pass the hydrogen sulfide through the reaction medium. Where the reaction is carried out in a pressure vessel, the hydrogen sulfide is suitably injected as a liquid or gas.

The acid acts as a catalyst in the process of the invention; suitably, from 0.1 to 1,000 mole percent, preferably from 0.5 to 20 mole percent, based on the starting compound of the formula I, are used.

The strong acids used are preferably inorganic acids which may be in the gaseous, liquid or solid state, depending on the particular process variant. Strong organic acids, e.g., formic acid, acetic acid and citric acid, may also be used.

The reaction according to the invention may be carried out as a gas phase reaction or as a liquid phase reaction, in a one-phase or two-phase system, and in one step or two steps.

Examples of suitable acids for the homogeneous reaction in the gas phase are the hydrogen halides, e.g., hydrogen chloride and hydrogen bromide, and the organic acids which are gaseous under the reaction conditions, e.g., formic acid, acetic acid and propionic acid, although the last two acids give lower conversions.

Examples of suitable acids for heterogeneous catalysis of the gas phase reaction are phosphoric acid, $H_3PO_4$ or sulfuric acid on ceramic carriers, e.g. aluminum oxide or silicon dioxide. Solid acids, e.g., sodium bisulfate or sodium dihydrogen phosphate, on ceramic carriers also act as catalysts.

Acids which may be used for the liquid phase reaction are phosphoric acid, sulfuric acid, formic acid and sulfonic acids, e.g., benzenesulfonic acid or p-toluenesulfonic acid, as well as solutions of hydrogen chloride, hydrogen bromide and sodium bisulfate in water and in lower alcohols, e.g., methanol, ethanol, isopropanol, n-propanol and butanol. Strongly acid ion exchangers, which may be regarded as solid acids, also catalyze the liquid phase reaction and may be used as strong acids. A further strong acid, for the purposes of the invention, is a buffer solution, e.g., a Sörensen citrate buffer of pH 1.2.

Elevated process temperatures are from 50° to 320° C, the choice of suitable temperature range depending on the process variant.

In a suitable embodiment, the starting material is reacted with hydrogen sulfide in the presence of a strong acid, at from 50° to 120° C, preferably from 60° to 100° C, in accordance with one of the following one-step variants:

1. As a single liquid phase, at atmospheric pressure, by reacting the 2,5-dialkoxy-3-formyl-tetrahydrofuran with a stream of hydrogen sulfide in acid alcoholic solution or acid aqueous-alcoholic solution. Preferred acids for this embodiment are hydrogen chloride, hydrogen bromide and sulfuric acid and preferred alcohols are methanol, isopropanol and n-propanol.
2. As a single liquid phase under superatmospheric pressure, the pressure being the autogeneous pressure under the process conditions and normally not exceeding 20 atmospheres gauge, by heating 2,5-dialkoxy-3-formyl-tetrahydrofuran, in acid aqueous-alcoholic solution, with from 0.75 to 1.25 mole equivalents of hydrogen sulfide in a pressure vessel, the alcohols named under 1. being preferred solvents.
3. As a two-phase liquid system under atmospheric pressure, by emuslifying 2,5-dialkoxy-3-formyl-tetrahydrofuran, as such or as a solution in a solvent (preferred solvents being those of low dipole moment, such as aromatic hydrocarbons, e.g., benzene or toluene) in aqueous acid, whilst passing in a stream of hydrogen sulfide. Suitable aqueous acids in this embodiment are, inter alia, hydrohalic acids, sulfuric acid, phosphoric acid and citric acid. The stream of hydrogen sulfide and any steam which may be passed in during the reaction can entrain the resulting 3-thenal from the reaction mixture.
4. In a further suitable one-step embodiment of the process, the reaction is carried out in the gas phase; the 2,5-dialkoxy-3-formyl-tetrahydrofuran vapor, in excess hydrogen sulfide, is reacted with strong acid at from 200° to 320° C, preferably at from 220° to 280° C,
   a. in the case of heterogeneous catalysis, by passing the gas mixture over an acid catalyst preferably consisting of phosphoric acid on silicon dioxide, or
   b. in the case of homogeneous catalysis, by injecting preferably from 5 to 20 mole percent of acid, especially hydrogen chloride, hydrogen bromide or formic acid, into the reactive gas mixture and employing temperatures of from 200° to 280° C, preferably from 220° to 250° C, and, if appropriate, using an inert carrier gas, e.g., nitrogen or argon, as a diluent. As a rule, from 100 to 1,000 mole percent of hydrogen sulfide, based on starting material, are employed.

In addition to a one-step reaction of 2,5-dialkoxy-3-formyl-tetrahydrofuran with hydrogen sulfide and acid, a two-step method is also feasible.

In a suitable two-step variant, 2,5-dialkoxy-3-formyl-tetrahydrofuran is reacted with from 0.9 to 1.5 equivalents of hydrogen sulfide at from 50° to 120° C, preferably at from 80° to 100° C, in a pressure vessel. The second step is to distil the resulting oily intermediate, after addition of acid, to give 3-thenal. A suitable method is to obtain the thenal from the oil in methanol in the presence of aqueous acid, e.g., 5 N sulfuric acid, at, preferably, from 60° to 100° C.

In a preferred two-step reaction, the 2,5-dialkoxy-3-formyl-tetrahydrofuran is reacted in aqueous solution with from 0.9 to 1.3 equivalents of hydrogen sulfide at from 60° to 110° C, preferably at from 80° to 100° C, and the thenal is then produced at from 80° to 100° C in the presence of, e.g., concentrated aqueous hydrochloric acid.

In another embodiment of the two-step method, the 2,5-dialkoxy-3-formyl-tetrahydrofuran, in acid aqueous solution or acid aqueous-alcoholic, especially aqueous-methanolic, solution, is heated to from 30° to 50° C until the exothermic reaction has subsided, and the product is then reacted with from 0.7 to 1.3 equivalents of hydrogen sulfide at elevated temperatures, preferably at from 80° to 100° C, in a pressure vessel, to give 3-thenal.

It is presumed that the exothermic character of the solution process in the acid medium is attributable to solvation and solvolysis of the starting compound. The following intermediates appear possible:

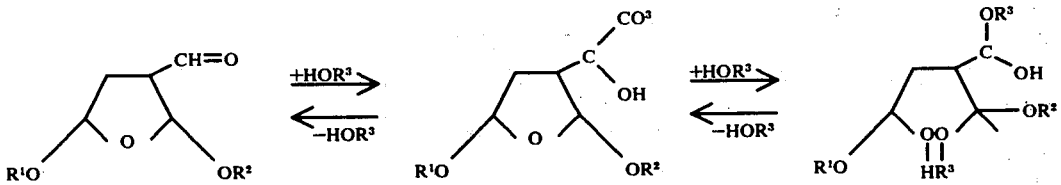

3-Thenal is a key compound in the synthesis of the highly active antibiotic 6-[(−)-α-amino/3-thienyl-acetamido]-penicillanic acid (U.S. Pat. 3,342,677). 3-Thenyl structural elements are also contained in other recent antibiotics (e.g., Netherlands Pat. No. 7,117,790 and Belgian Pat. No. 775,781). 3-Thenal could not be manufactured in sufficient quantity by earlier processes; the invention makes the compound available in industrial quantities and enables it to be used for further novel applications.

As described in Org. Synth. Coll. Vol. IV, 918, 3-thenal has previously been synthesized by various processes:

The preparation of 3-thenal from 3-methylthiophene by bromination with N-bromosuccinimide by a free-radical mechanism, followed by reaction with hexamethylenetetramine, is expensive and involved. Because of safety hazards, this process is only suitable for the synthesis of minor amounts of the substance.

The preparation of 3-thenal from thiophene via tetraiodothiophene, partial reduction and Grignard reaction with ethyl o-formate is handicapped by the number of reaction steps involved and the low yield.

3-Thenal may also be prepared by reduction of thiophene-3-carboxylic acid anilide with lithium aluminum hydride. However, 3-thenal is itself the preferred starting material for thiophene-3-carboxylic acid (Org. Synth. Coll. Vol. IV, 920).

The preparation of 3-thenal from 3-bromothiophene with n-butyl-lithium and dimethylformamide has the disadvantage that the starting material must be prepared from thiophene-2-carboxylic acid in several steps and using two-molar amounts of mercury salts.

As a result of the difficulties of the conventional processes for the manufacture of 3-thenal, the latter is difficult to obtain and only available in limited amounts, and furthermore the commercially available products in most cases still contain about 15% of 2-thenal.

The process of the invention for the manufacture of 3-thenal is superior to the conventional processes in that 3-thenal may be obtained free from 2-thenal, in good yield, from readily accessible starting materials, by a reaction which is easy to carry out.

A large number of side reactions is conceivable when reacting 2,5-dialkoxy-3-formyl-tetrahydrofuran with hydrogen sulfide and acid; examples are the formation of an acyclic trialdehyde and its self-condensation, aromatization to give furanaldehyde, and formation of oligomeric thioaldehydes containing tetrahydrofuran, furan or thiophene radicals. It is for this reason that the feasibility and yields of the process of the invention are surprising to those skilled in the art.

The examples which follow illustrate the invention. Where the examples do not describe a working-up procedure, the yields have been determined by gas chromatography (PERKIN-ELMER Gas Chromatograph F 20 H, 2 m OV 17, 150° C).

EXAMPLE 1

A boiling mixture of 100 ml of n-propanol and 1.0 ml of concentrated HCl is mixed with a stream of $H_2S$ (130 g/hour) by means of a Vibro-mixer. 10 g of 2,5-dimethoxy-3-formyl-tetrahydrofuran are added dropwise in the course of 10 minutes, the stream of $H_2S$ is reduced to 32 g/hour and the mixture is boiled for a further 2 hours.

The batch is worked up by partitioning between benzene and water. Drying the organic phase, and fractional distillation in vacuo, gives 2.8 g of 3-thenal (40% of theory).

EXAMPLE 2

10 g of 2,5-dimethoxy-3-formyl-tetrahydrofuran are reacted with $H_2S$ in a boiling mixture of 100 ml of iso-propanol and 3.0 ml of half-concentrated HBr, by the method described in Example 1.

On working up as in Example 1, 2.3 g of 3-thenal (33% of theory) are obtained.

EXAMPLE 3

10 g of 2,5-dimethoxy-3-formyl-tetrahydrofuran are added in the course of 10 minutes to a boiling mixture of 100 ml of iso-butanol and 1.0 ml of concentrated HCl, whilst being mixed with a stream of $H_2S$ (130 g/hour). After boiling for 1 hour under a slower stream of $H_2S$ (32 g/hour), the mixture is allowed to cool to 90° C, 10 ml of $H_2O$ are added to hydrolyze acetals and the batch is kept at 90° C for 1 hour. It contains 3.4 g of 3-thenal (48% of theory).

EXAMPLE 4

80 ml of methanol are added to 32 g of 2,5-dimethoxy-3-formyl-tetrahydrofuran at from 2° to 8° C. A mixture of 1.0 ml of concentrated HCl and 20 ml of methanol is added dropwise at from 2° to 4° C, the solution is transferred to a tantalum-lined 250 ml steel bomb, 7 g of $H_2S$ are forced in and the mixture is heated at 80° C for 6 hours, whilst shaking. The red-brown reaction solution contains 9.5 g of 3-thenal (42% of theory).

EXAMPLE 5

An ice-cooled solution of 1.0 ml of concentrated HCl and 1.0 ml of $H_2O$ in 50 ml of iso-propanol is added to 43 g of 2,5-diisopropoxy-3-formyl-tetrahydrofuran dissolved in 50 ml of ice-cooled iso-propanol. The mixture is shaken with 8.5 g of $H_2S$ for 6 hours at 100° C in a tantalum-lined 250 ml steel bomb. The reaction solution contains 7.5 g of 3-thenal (33% of theory).

EXAMPLE 6

A mixture of 1.0 ml of concentrated HCl and 1.0 ml of $H_2O$ in 50 ml of ethanol is added to 54 g of 2,5-diisoamyloxy-3-formyl-tetrahydrofuran dissolved in 50 ml of ethanol. The batch is shaken for 6 hours at 120° C with 5.0 g of $H_2S$ in a 250 ml tantalum-lined steel bomb. The reaction solution contains 8.2 g of 3-thenal (37% of theory).

EXAMPLE 7

An ice-cooled solution of 50 ml of concentrated HCl and 5.0 ml of $H_2O$ in 250 ml of n-propanol is added to 160 g of 2,5-dimethoxy-3-formyl-tetrahydrofuran dissolved in 250 ml of n-propanol. The mixture is introduced into a 3 l glass insert of a bomb intended for rolling on a sloping roller stand, 36 g of $H_2S$ are forced in and the bomb is rolled for 6 hours at 80° C. After decanting from 13.8 g of resin, the solution, which has been concentrated to 300 ml, is partitioned between benzene and water, the organic phase is dried, and 52 g of 3-thenal (46% of theory) are obtained by distillation.

EXAMPLE 8

32 g of 2,5-dimethoxy-3-formyl-tetrahydrofuran are added dropwise at from 2° to 4° C to a mixture of 2 ml of 6 N $H_2SO_4$, 3 ml of $H_2O$ and 90 ml of MeOH and the mixture is shaken with 7.0 g of $H_2S$ in a 250 ml tantalum-lined steel bomb for 6 hours at 100° C. The reaction solution contains 11 g of 3-thenal (49% of theory).

EXAMPLE 9

10 ml of "Lewatit S 100 active" ion exchanger (Bayer AG, Leverkusen) are washed with MeOH and 32 g of 2,5-dimethoxy-3-formyl-tetrahydrofuran are added to the ion exchanger in 100 ml of methanol and 5.6 ml of $H_2O$ at from 2° to 4° C. The mixture is shaken with 7.0 g of $H_2S$ for 6 hours at 100° C in a 250 ml steel bomb. The solution contains 7.3 g of 3-thenal (33% of theory).

EXAMPLE 10

113 g of 2,5-dimethoxy-3-formyl-tetrahydrofuran are emulsified, in the course of 50 minutes, with 380 ml of 1 N HCl and a stream of $H_2S$ (70 g/hour) in a 30 ml reaction vessel at 72° C. The discharged mixture is allowed to react further for 1 hour in a receiver containing 300 ml of $C_6H_6$ and 100 ml of 1 N HCl at 62° C, and to separate into phases. The organic phase is washed neutral with water and on distillation gives 44 g of 3-thenal (55% of theory) boiling at 48° – 50° C/0.5 mm Hg.

EXAMPLE 11

320 g of 2,5-dimethoxy-3-formyl-tetrahydrofuran, dissolved in 1.3 l of benzene, are emulsified, in the course of 300 minutes, with 1.6 l of 1 N HCl and a stream of $H_2S$ (54 g/hour) in a 30 ml reaction vessel at from 61° to 63° C. The discharged material is allowed to react further for 1 hour in a receiver at from 64° to 66° C, with back-mixing. The organic phase is washed neutral and distilled, to give 110 g of 3-thenal (49% of theory).

EXAMPLE 12

80 g of 2,5-dimethoxy-3-formyl-tetrahydrofuran, dissolved in 330 ml of $C_6H_6$, are emulsified, in the course of 90 minutes, with a stream of $H_2S$ (54 g/hour) and 400 ml of 1 N $H_2SO_4$ in a 30 ml reaction vessel at 60° C. The discharged material is allowed to react further for 1 hour at 64° C. The organic phase is washed neutral and distilled, to give 22 g of 3-thenal (39% of theory).

EXAMPLE 13

100 ml of a buffer solution of pH 1.2 (Sörensen citrate buffer) are emulsified with 20 ml of xylene and a stream of $H_2S$ (130 g/hour) at 85° C, using a Vibromixer. In the course of 60 minutes, 6.0 g of 2,5-dimethoxy-3-formyl-tetrahydrofuran are added dropwise and the mixture is allowed to react further for 15 minutes. The xylene phase contains 1.4 g 3-thenal (31% of theory).

EXAMPLE 14

Steam (150 g/hour) and $H_2S$ (130 g/hour) are passed into 100 ml of boiling 0.1 N HCl and 10 g of 2,5-dimethoxy-3-formyl-tetrahydrofuran are introduced in the course of 10 minutes. After shutting off the stream of $H_2S$, the steam distillation is continued for 30 minutes. Extraction of the distillate with $CH_2Cl_2$ gives 3.0 g of 3-thenal (43% of theory).

EXAMPLE 15

32 g of 2,5-dimethoxy-3-formyl-tetrahydrofuran are added to 100 ml of 1 N $H_2SO_4$ at from 6° to 8° C and the mixture is shaken with 6.5 g of $H_2S$ for 6 hours at 80° C in a steel bomb of 250 ml capacity. The whole batch is then partitioned between $CHCl_3$ and $H_2O$. The organic phase is washed neutral and is found to contain 2.5 g of 3-thenal (10% of theory).

EXAMPLE 16

160 g of 2,5-dimethoxy-3-formyl-tetrahydrofuran are shaken with 34 g of $H_2S$ for 6 hours at 80° C in a 250 ml steel bomb, giving 194 g of a red-brown oil. 14.3 g of this oil are heated with 140 mg of p-toluenesulfonic acid to 200° C in 30 minutes at atmospheric pressure, during which time 0.4 g of 3-thenal (5% of theory) pass over in the 4.5 g of distillate.

EXAMPLE 17

16 g of red-brown oil from Example 16, in 50 ml of MeOH, are boiled with 2.0 ml of 6 N $H_2SO_4$ under reflux for 8 hours. The color deepens and 3.1 g of 3-thenal (33% of theory) are formed.

EXAMPLE 18

80 g of 2,5-dimethoxy-3-formyl-tetrahydrofuran are dissolved in 330 ml of ice water and reacted with a stream of $H_2S$ (28 g/hour) in the course of 40 minutes in a stirred reactor (of 30 ml capacity) which is kept at from 86° to 88° C. The material discharged from the reactor is run into a receiver in which 50 ml of 3.3 N HCl and 100 ml of $C_6H_6$ are stirred at 63° C and into which concentrated HCl (3.3 ml/minute) is introduced dropwise at the same time. The mixture is then stirred for 1 hour at 65° C and the benzene phase is separated off and washed neutral. The aqueous phase is extracted twice with 150 ml of $C_6H_6$. Fractional distillation of the dried organic phase gives 29 g of 3-thenal (52% of theory).

EXAMPLE 19

50 g of 2,5-dimethoxy-3-formyl-tetrahydrofuran are vaporized in 40 minutes at 250° C and passed, in a stream of $H_2S$ (23 l/hour), over a catalyst, at 280° C, which consists of 3.5 g of $H_3PO_4$ on 70 g of $Al_2O_3$ (extrudates of 4 mm diameter). When the steady state has been reached, the condensate contains 40% of 3-thenal.

EXAMPLE 20

10 g of 2,5-dimethoxy-3-formyl-tetrahydrofuran are vaporized in 20 minutes at 250° C and carried, in a stream of $H_2S$ (33 l/hour) into a reaction tube filled with glass beads and heated to 240° C, into which 5.0 ml of 85% strength formic acid are injected simultaneously with a second stream of $H_2S$ (20 l/hour) (residence time about 2 seconds). The condensate contains 10% of 3-thenal and 50% of the starting compound.

EXAMPLE 21

Example 20 is repeated using 12 ml of acetic acid instead of the formic acid; the condensate contains 1% of 3-thenal and 95% of starting compound.

EXAMPLE 22

100 g of 2,5-dimethoxy-3-formyl-tetrahydrofuran are vaporized in 100 minutes at 250° C and carried in a stream of $H_2S$ (23 l/hour) into an empty reaction tube, at 220° C, into which HCl gas (8 l/hour), in a second stream of $H_2S$ (20 l/hour), is injected simultaneously. Condensation with thorough cooling gives a distillate containing 35% of 3-thenal in the organic phase.

We claim:
1. A process for the manufacture of thiophen-3-aldehyde, which comprises reacting a 2,5-dialkoxy-3-formyl-tetrahydrofuran of the formula I

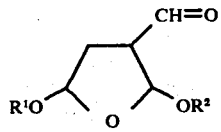

in which $R^1$ and $R^2$ may be identical or different and each is straight-chain or branched alkyl of 1 to 5 carbon atoms, with hydrogen sulfide in the presence of an acid whose pK in aqueous solution is at most 5.0 at elevated temperatures of from 50° to 320° C.

2. A process as set forth in claim 1, wherein a 2,5-dialkoxy-3-formyl-tetrahydrofuran is reacted, in acid alcoholic or acid aqueous-alcoholic solution, in the presence of hydrogen chloride, hydrogen bromide or sulfuric acid with a stream of hydrogen sulfide at from 50° to 120° C.

3. A process as set forth in claim 1, wherein a 2,5-dialkoxy-3-formyl-tetrahydrofuran of the formula I is reacted, in acid aqueous alcohol solution, in the presence of hydrogen chloride, hydrogen bromide or sulfuric acid with from 0.75 to 1.25 mole equivalents of hydrogen sulfide in a pressure vessel at from 50° to 120° C.

4. A process as set forth in claim 1, wherein a 2,5-dialkoxy-3-formyl-tetrahydrofuran of the formula I, is reacted by introducing hydrogen sulfide in the presence of aqueous hydrogen chloride, hydrogen bromide, sulfuric acid or phosphoric acid at from 50° to 120° C and the volatile reaction products are at the same time steam-distilled.

5. A process as set forth in claim 4 wherein said 2,5-dialkoxy-3-formyltetrahydrofuran of the formula I is dissolved in a solvent.

6. A process as set forth in claim 1, wherein the reaction is carried out in two steps, by reacting a 2,5-dialkoxy-3-formyl-tetrahydrofuran of the formula I, in the pure form or in solution, with hydrogen sulfide at from 60° to 110° C, followed by adding hydrogen chloride at from 80° to 100° C.

7. A process as set forth in claim 1, wherein a 2,5-dialkoxy-3-formyl-tetrahydrofuran of the formula I, as vapor, is reacted with hydrogen sulfide over phosphoric acid on silicon dioxide at from 200° to 320° C.

8. A process as set forth in claim 1, wherein a 2,5-dialkoxy-3-formyl-tetrahydrofuran of the formula I is reacted with excess hydrogen sulfide and with gaseous hydrogen chloride, hydrogen bromide or formic acid at from 200° to 320° C.

9. A process as set forth in claim 1, wherein the pK of the acid in aqueous solutions is less than 3.0.

10. A process as set forth in claim 1 wherein said acid is selected from the group consisting of hydrogen chloride, hydrogen bromide, phosphoric acid, sulfuric acid, formic acid, acetic acid, propionic acid, benzenesulfonic acid, p-toluenesulfonic acid, strongly acid ion exchanger, Sörensen citrate buffer of pH 1.2, phosphoric acid on aluminum oxide, phosphoric acid on silicon dioxide, sulfuric acid on aluminum oxide and sulfuric acid on silicon dioxide.

* * * * *